US012576028B2

(12) United States Patent
Wang et al.

(10) Patent No.: US 12,576,028 B2
(45) Date of Patent: Mar. 17, 2026

(54) PHARMACEUTICAL OR NUTRACEUTICAL SELF-EMULSIFYING SOLID DISPERSION COMPOSITION

(71) Applicant: HUANA GLOBAL BIOTECH CO., LTD., New Taipei City (TW)

(72) Inventors: Liang-Shun Wang, New Taipei City (TW); Chih-Chiang Yang, Taipei City (TW); Yu-Hsuan Lin, New Taipei City (TW); Ping-Chuan Fu, New Taipei City (TW)

(73) Assignee: HUANA GLOBAL BIOTECH CO., LTD., New Taipei City (TW)

( * ) Notice: Subject to any disclaimer, the term of this patent is extended or adjusted under 35 U.S.C. 154(b) by 0 days.

(21) Appl. No.: 18/098,518

(22) Filed: Jan. 18, 2023

(65) Prior Publication Data

US 2023/0149308 A1     May 18, 2023

Related U.S. Application Data

(63) Continuation of application No. 16/716,039, filed on Dec. 16, 2019, now abandoned.

(60) Provisional application No. 62/857,926, filed on Jun. 6, 2019.

(51) Int. Cl.
| | |
|---|---|
| *A61K 9/10* | (2006.01) |
| *A61K 31/355* | (2006.01) |
| *A61K 47/02* | (2006.01) |
| *A61K 47/10* | (2017.01) |
| *A61K 47/26* | (2006.01) |
| *A61K 47/40* | (2006.01) |
| *A61K 47/44* | (2017.01) |

(52) U.S. Cl.
CPC .............. *A61K 9/10* (2013.01); *A61K 31/355* (2013.01); *A61K 47/02* (2013.01); *A61K 47/10* (2013.01); *A61K 47/26* (2013.01); *A61K 47/40* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 6,562,372 B1 | 5/2003 | Yokoi et al. |
| 2003/0072798 A1 | 4/2003 | Schwarz |
| 2009/0087501 A1 | 4/2009 | Cummins |
| 2016/0220593 A1 | 8/2016 | Anastassov et al. |

FOREIGN PATENT DOCUMENTS

| | | |
|---|---|---|
| JP | 63-243034 A | 10/1988 |
| JP | 5249568 B2 | 7/2013 |

OTHER PUBLICATIONS

Alqahtani, S., et al., The AAPS Journal 15(3): 684-695 (2013). (Year: 2013).*
Shen, L., et al., Surface Science 605: 494-499 (2011). (Year: 2011).*
Kerwin, B., Journal of Pharmaceutical Sciences 97: 2924-2935 (2008). (Year: 2008).*
Kollidon, obtained from the Internet at file:///C:/Users/dcoughlin/Downloads/-kollidon-25_technical_information.pdf on May 31, 2024. (Year: 2024).*
Mohamad, N.V., Pharmaceuticals 16: 1403 (2023). (Year: 2023).*
International Search Report and Written Opinion of the International Searching Authority dated Feb. 28, 2020 for Application No. PCT/US19/66491.
Polyoxyethylene sorbitan monooleate, accesses on the Internet from <https://pubchem.ncbi.nlm.nih.gov/compound/Polyoxyethylene-sorbitan-mono-oleate#section=DSSTox-Su on Feb. 5, 2022. (Year: 2022).

* cited by examiner

*Primary Examiner* — David J Blanchard
*Assistant Examiner* — Daniel F Coughlin
(74) *Attorney, Agent, or Firm* — Birch, Stewart, Kolasch & Birch, LLP

(57) ABSTRACT

The present invention pertains to a pharmaceutical, or nutraceutical, "self-emulsifying solid dispersion" composition for oral administration which contains (a) a drug or a nutraceutical that is water-insoluble or poorly water-soluble; (b) at least one surfactant; (c) one carrier selected from the group consisting of silicic acid, a silicate, or any combination thereof; and (d) at least one carbohydrate filler.

2 Claims, 4 Drawing Sheets

PHARMACEUTICAL OR NUTRACEUTICAL SELF-EMULSIFYING SOLID DISPERSION COMPOSITION

CROSS REFERENCE TO RELATED APPLICATIONS

This application is a Continuation of U.S. application Ser. No. 16/716,039, filed Dec. 16, 2019, which claims the benefit of and priority to U.S. Provisional Application Ser. No. 62/857,926, filed Jun. 6, 2019, which are incorporated herein by reference in its entirety.

FIELD OF THE INVENTION

The present invention relates to a pharmaceutical or nutraceutical self-emulsifying solid dispersion (SESD) composition.

BACKGROUND OF THE INVENTION

There are about 40% of approved drugs and nearly 90% of the developmental pipeline drugs consisting of poorly soluble molecules. Several marketed drugs suffer from poor solubility, low permeability, rapid metabolism and elimination from the body along with poor safety and tolerability.

On the other hand, bioactive agents such as nutraceuticals may also have low or variable bioavailability, which may limit their effectiveness and lead to variations in their efficacy. For example, vitamin E, which is essential component of the human diet because the body cannot manufacture vitamin E, has been known to support fertility and have antioxidant activities. Moreover, vitamin E deficiency has been associated with oxidant stress-related pathologies, such as age-related cataract, irradiation injury and anemia. Natural vitamin E is a group of eight fat soluble compounds that include four tocopherols and four tocotrienols (T3s). But the abundance of $\alpha$-tocopherol in the human body attracts so much attention that leads to the neglection of non-tocopherol vitamin E molecules as topics for basic and clinical research. Tocopherol has molecular structure with saturated isoprenoid side chain, or tail. T3 differ structurally from tocopherols by the presence of three trans double bonds in the hydrocarbon tail, or unsaturated tail. Recent studies indicate that the T3 subfamily of natural vitamin E possess effective neuroprotective, anti-cancer, anti-inflammation, and cholesterol lowering properties that are often not exhibited by tocopherols.

However, the lack of understanding on the bioavailability and behavior of T3 in the human system hurdles the advancement of T3. Although vitamin E in general has been well studied for their absorption and metabolic fate, the plasma concentrations of T3s were found to be much lower compared to tocopherols. Therefore, it is important to improve the absorption and bioavailability, thereby enhancing therapeutic efficacy of T3.

BRIEF SUMMARY OF THE INVENTION

Accordingly, the present invention provides a pharmaceutical or a nutraceutical, "self-emulsifying solid dispersion" (SESD) composition for oral administration comprising a drug or a nutraceutical that is water-insoluble or poorly water-soluble (hydrophobic).

It is an object of the present invention to provide a pharmaceutical or a nutraceutical SESD composition for oral administration, comprising: (a) a drug or a nutraceutical that is water-insoluble or poorly water-soluble; (b) at least one surfactant; (c) one carrier selected from the group consisting of silicic acid, a silicate, and any combination thereof; and (d) at least one carbohydrate filler.

In some embodiments of the present invention, the drugs or nutraceuticals are selected from the group consisting of tocotrienols (T3s), tocopherols, vitamins A, D, K and 0-carotene or other hydrophobic medicines or extracts.

In one example of the present invention, the drug or the nutraceutical comprises at least one of T3s.

In some embodiments of the present invention, the surfactant is selected from the group consisting of polysorbate (TWEEN®), sorbitan fatty acid ester (Span), polyethylene glycol (PEG), polyoxyl 35 castor oil, etc. and any combination thereof.

In some embodiments of the present invention, the carbohydrate filler is selected from the group consisting of lactose, isomalt, cyclodextrin, dextrates, isomaltodextrin, maltodextrins, etc., and any combination thereof.

In some embodiments of the present invention, the pharmaceutical or nutraceutical SESD composition further comprises (e) at least one binder and (f) at least one lubricant.

In some embodiments of the present invention, the pharmaceutical or nutraceutical SESD composition further comprises (e) at least one binder or (f) at least one lubricant.

It is another object of the present invention to provide a delivery system for a water-insoluble or poorly water-soluble (hydrophobic) drug or nutraceutical, which comprises one carrier selected from the group consisting of silicic acid, a silicate, and any combination thereof, at least one surfactant; and at least one carbohydrate filler.

It is to be understood that both the foregoing general description and the following detailed description are exemplary and explanatory only and are not restrictive of the invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawing embodiments which are presently preferred.

In the drawings.

PVP K30; FT5, starch+PVP K30. Data is presented as means±SD, n=3 for each group; *, p<0.05; , p<0.01; *, p<0.001.

Figure 4:
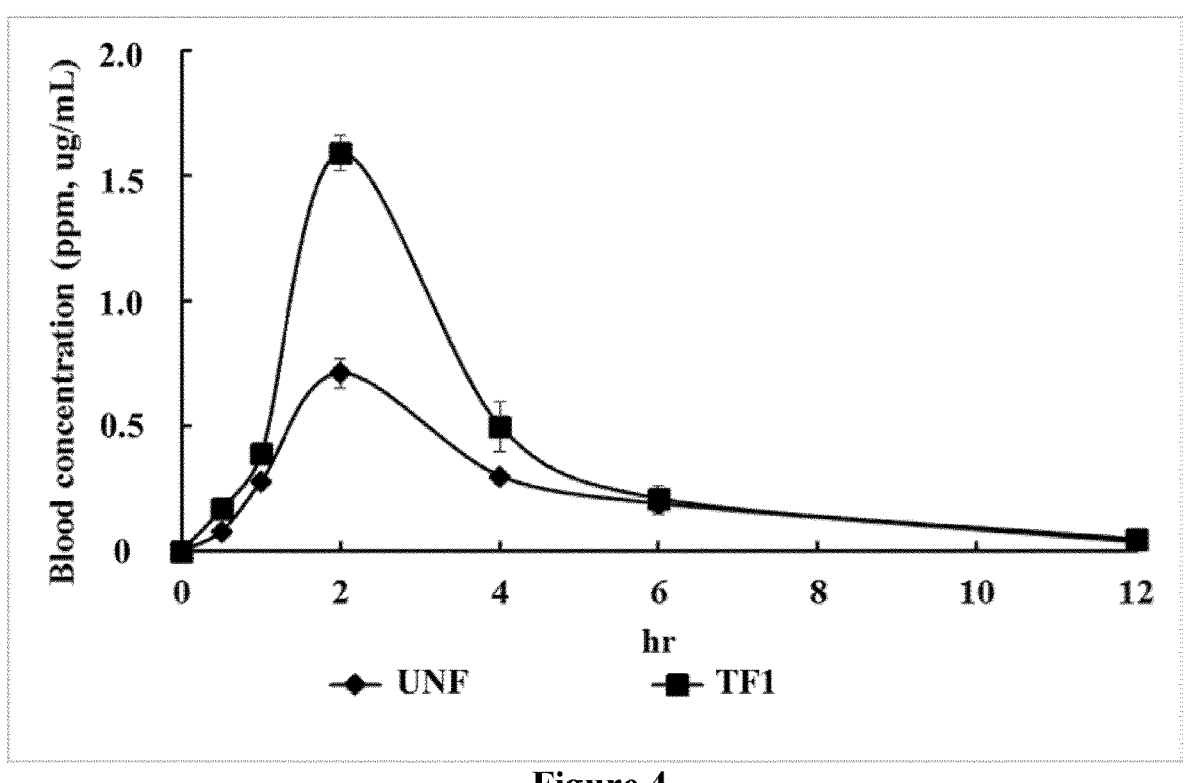

FIG. 4 shows the pharmacokinetic (PK) study of UNF and FT1 in Sprague Dawley (SD) rats. The T3 bioacceptability of FT1 was markedly superior to that of UNF in pharmacokinetic study, including Tmax, Cmax and AUC (Area Under Curve). UNF, unformulated T3s; FT1, isomalt+wet granulation. Cmax, maximum blood drug concentration; Tmax, time to reach Cmax; AUC (Area Under Curve), The area of under the concentration-time curve.

DETAILED DESCRIPTION OF THE INVENTION

The above summary of the present invention will be further described with reference to the embodiments of the following examples. However, it should not be understood that the content of the present invention is only limited to the following embodiments, and all the inventions based on the above-mentioned contents of the present invention belong to the scope of the present invention.

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

The present invention provides a pharmaceutical, or a nutraceutical, "Self-emulsifying solid dispersion" (SESD) composition for oral administration, comprising: (a) a drug or a nutraceutical that is water-insoluble or poorly water-soluble; (b) at least one surfactant; (c) one carrier selected from the group consisting of silicic acid, a silicate, or any combination thereof; and (d) at least one carbohydrate filler.

In some embodiments of the present invention, the pharmaceutical or nutraceutical, SESD composition further comprises (e) at least one binder and (f) at least one lubricant.

In some embodiments of the present invention, the pharmaceutical or nutraceutical, SESD composition further comprises (e) at least one binder or (f) at least one lubricant.

It is found that the pharmaceutical, or nutraceutical, SESD composition according to the invention could significantly increase solubility, bioaccessibility, and absorption.

On the other hand, the present invention also provides a delivery system for a water-insoluble or poorly water-soluble drug or nutraceutical, which comprises one carrier selected from the group consisting of silicic acid, a silicate, or any combination thereof; at least one surfactant; and at least one carbohydrate filler.

The term "self-emulsifying solid dispersion" (SESD) defined as the dispersion and self-emulsifying effect of one or more active ingredient in a carrier or matrix at solid state, is an efficient strategy for improving dissolution of the water-insoluble or poorly water-soluble (hydrophobic) drugs or nutraceuticals for enhancement of their bioavailability.

By "poorly water soluble" or "hydrophobic", it is meant that the drugs or nutraceuticals have less than 10 mg/mL solubility, and preferably less than 0.1 mg/mL, in the physiological pH range at 25° C. The solubility can be measured in a standard method.

In some embodiments of the present invention, the drug may be used directly as a medicament that remains free base or acid, or as a form of a pharmaceutically acceptable salt that may be prepared by known methods. Acid addition salts include but are not limited to, for example, hydrochloric acid, hydrobromic acid, sulfuric acid, mineral acids such as phosphoric acid, acetic acid, citric acid, tartaric acid, maleic acid, succinic acid, fumaric acid, p-toluenesulfonic acid, benzene sulfonic acids, or salts with organic acids such as methane sulfonic acid. Base addition salts include but are not limited to, for example, sodium salts, lithium salts, alkali metal salts such as potassium salts, aluminum salts, calcium salts, alkaline earth metal salts such as magnesium salt, or an ammonium salt.

The pharmaceutical or nutraceutical SESD composition of the present invention may be formulated into various dosage forms, including tablets, capsules, powders, granules, dry syrups and the like. In a certain embodiment, the pharmaceutical or nutraceutical SESD composition of the present invention is in a form of granules, or a solid form.

In the present invention, the drug, or the nutraceutical, is selected from the group consisting of T3s, tocopherols, vitamins A, D, or K, β-carotene or other hydrophobic medicines or extracts.

In one example of the present invention, the drug or the nutraceutical comprises at least one T3.

In the present invention, the content of the drug or the nutraceutical is 1% to 60% by weight. Preferably, the content of the drug or nutraceutical is 1% to 20% by weight.

The term "surfactant" as used herein refers to a class of substances with strong surfactivity which can significantly reduce the surface tension of the liquid. Suitable surfactants include nonionic, cationic, and anionic surfactants that can be synthetic or natural. The surfactants included in the present invention will increase the wetting and solubilization of the drug or nutraceutical in a formulation when used together. Examples of surfactants include, but not limited to, ammonium lauryl sulfate, sodium lauryl sulfate (SDS), sodium laureth sulfate, also known as sodium lauryl ether sulfate (SLES), sodium myreth sulfate, dioctyl sodium sulfosuccinate, perfluorooctanesulfonate (PFOS), perfluorobutanesulfonate, alkyl ether phosphate, sodium stearate, sodium lauroylsarcosinate, perfluorononanoate, perfluorooctanoate (PFOA or PFO), octenidinedihydrochloride, permanently charged quaternary ammonium cation, cetyltrimethylammonium bromide (CTAB) (i.e., hexadecyl trimethyl ammonium bromide), cetyltrimethylammonium chloride (CTAC), cetylpyridinium chloride (CPC), polyethoxylated tallow amine (POEA), benzalkonium chloride (BAC), benzethonium chloride (BZT), 5-bromo-5-nitro-1,3-dioxane, dimethyldioctadecylammonium chloride, dioctadecyldimethylammonium bromide (DODAB), CHAPS (3-[(3-cholamidopropyl)dimethylammonio]-1-propanesulfonate), cocamidopropylhydroxysultaine, cocamidopropylbetaine, lecithin, cetyl alcohol, stearyl alcohol, cetostearyl alcohol (consisting predominantly of cetyl and stearyl alcohols), oleyl alcohol, octaethylene glycol monododecyl ether, pentaethylene glycol monododecyl ether, polyoxypropylene glycol alkyl ethers, glucoside alkyl ethers, decyl glucoside, lauryl glucoside, octylglucoside, polyoxyethylene glycol octylphenol, Triton X-100, polyoxyethylene glycol alkylphenol ethers, Nonoxynol-9, glyceryl laurate, polysorbates like polysorbate 20 (TWEEN® 20), polysorbate 40 (TWEEN® 40), polysorbate 60 (TWEEN® 60), polysorbate 65 (TWEEN® 65), polysorbate 80 (TWEEN® 80), Sorbitan fatty acid ester 20 (Span 20), Sorbitan fatty acid ester 40 (Span 40), Sorbitan fatty acid ester 65 (Span 65), Sorbitan fatty acid ester 80 (Span 80), sorbitan alkyl esters, cocamide MEA, cocamide DEA, dodecyl dimethylamine oxide, and block copolymers of polyethylene glycol and polypropylene glycol, or mixtures of one or more thereof.

In the present invention, the surfactant is selected from the group consisting of polysorbate (TWEEN®), sorbitan fatty acid ester (Span), polyethylene glycol (PEG), polyoxyl 35 castor oil, and any combination thereof. Preferably, the surfactant is polysorbate 80, polysorbate 20, sorbitan fatty acid ester, polyethylene glycol 200, or polyoxyl 35 castor oil. The surfactant may be 0.1% to 10% by weight, preferably 1% to 5%.

According to the present invention, the composition also can comprise a carrier (e.g., a pharmaceutically or dietetically acceptable carrier). The carrier can be any suitable carrier or mixture of carriers.

The term "carrier" as used herein refers to a substance designed to interact with, and enhance the properties, of active pharmaceutical ingredients. For example, granules with high-quality fluidity and low moisture absorption are ideal for tableting and capsule filling. Examples of carrier include, but not limited to, silicon dioxide, starch, lactose, sucrose, sorbitol, talc, stearic acid, magnesium stearate, and mixtures thereof. In one embodiment of the present invention, the carrier is 1% to 40% by weight, preferably 1% to 20% by weight.

The term "filler" as used herein refers to a substance adding bulk to products making very small active ingredient components easy for consumer to take. Preferably said filler is an organic compound, an inorganic compound, or a protein.

Examples of organic filler include, but not limited to, lactose (e.g., spray dried lactose, lactose α-, β-lactose, Monohydrate® tablet, various grades of permanent Monohydrate®, micro Monohydrate® or Fast-Floc®) microcrystalline cellulose (various grades of Albi Cell®, El Sema®, Viva Cell®, Ming Tai® or Solka-Floc®), hydroxypropyl-cellulose, L-hydroxypropyl cellulose (jeochi cyclic), hydroxypropyl methyl cellulose (HPMC) (such as Shin-Etsu's Methocel E, F and K, metol Los SH, e.g., Methocel E grades of 4,000 cps and metol Los 60 SH; 4,000 cps grade of Methocel F and metol Los 65 SH; 4,000, 15,000 and 100,000 cps grades of Methocel K; and the 4,000, 15,000, 39,000 and 100,000 grades of metol Los 90 SH), methyl-cellulose polymers (e.g. Methocel a, Methocel A4C, Methocel A15C, Methocel A4M), hydroxyethyl cellulose, car-boxymethyl cellulose Sodium, carboxymethyl ethyl cellulose and other cellulose derivatives, sucrose, agarose, sorbitol, mannitol, isomalt, dextrins, maltodextrins, cyclo-dextrin, isomaltodextrin, and starch or modified starch (potato starch, including corn starch and rice starch).

Examples of inorganic filler include, but not limited to, inorganic pigments such as titanium dioxide, zinc oxide, antimony oxide, magnesium oxide, fly ash, red oxide, yellow oxide, lemon chrome and cobalt blue; powders of metals including titanium, copper, brass, gold and stainless steel; carbonates such as calcium and magnesium carbonates; phosphates such as calcium and lead phosphates; silica and silicates such as clay and glass particles; chromates such as lead chromate; metal salts such as silver chloride; inert filler materials such as titanates and talc; ferrites; aluminum hydrates; and the like. Of particular interest are powders of metals and metal alloys such as aluminum, cobalt, iron, copper, nickel, chromium, zinc, palladium, silver, ruthenium, platinum, gold, rhodium, lead and alloys of these metals. Also of interest are the oxides of such metals, particularly magnetic oxides such as iron, nickel, cobalt or alloys thereof, as well as oxides of other elements such as titanium dioxide and silica.

Examples of protein filler include, but not limited to, collagen, hyaluronic acid (hyaluronan), and gelitacollagel.

In some embodiments of the present invention, the carbohydrate filler is selected from the group consisting of lactose, isomalt, cyclodextrin, dextrates, isomaltodextrin, maltodextrins, and any combination thereof. The carbohydrate filler is 15% to 90% by weight, preferably 40% to 90% by weight. In one embodiment of the present invention, the carbohydrate filler is 50% to 60%, 60% to 70%, 70% to 80%, or 80% to 90% by weight.

The term "binder" as used herein refers to an excipient that is formulated to act as an adhesive to literally "bind together" powders, granules and other dry ingredients to impart to the product the necessary mechanical strength. Commonly used in wet granulation, binders are added to create a more effective and predictable granule formation. Examples of binder include, but not limited to, surfactants block copolymers EO/PO, polyvinyl alcohols, polyvinylpyr-rolidones, polyacrylates, polymethacrylates, polybutenes, polyisobutylenes, polystyrenes, polyethyleneamines, poly-ethyleneamides, polyethyleneimines (Lupasol®, Polymin), polyethers, polyurethanes, poly (vinyl acetates), tylose and copolymers of these polymers.

In one preferred embodiment of the present invention, the binder is polyvinylpyrrolidones.

The term "lubricant" as used herein refers to a substance preventing adherence of granule/powder to punch die/faces and promote smooth ejection from the die after compaction. Lubricants can also be used when compression is not involved such as in powder blends for filling into capsules to prevent adherence of granule/powder to equipment surfaces and Dosator mechanisms and coating the surface of multi-particulate dosage forms to inhibit agglomeration of individual particles. Examples of lubricant include, but not limited to, stearic acid, magnesium stearate, calcium stearate or stearic acid, talc, waxes and glycerides, light oil of a different metal, PEG, glyceryl behenate, colloidal silica, vegetable hardened oils, corn starch, sodium stearyl fumarate and the like, polyethylene glycols, alkyl sulfates, sodium benzoate, and sodium acetate.

The term "subject" as used herein includes human or non-human animals, such as companion animals (e.g. dogs, cats, etc.), farm animals (e.g. cattle, sheep, pigs, horses, etc.), or experimental animals (e.g. rats, mice, guinea pigs, etc.).

The term "effective amount" as used herein refers to an amount of a pharmaceutical agent or a nutraceutical which, as compared to a corresponding subject who has not received such amount, results in an effect in treatment, healing, prevention, or amelioration of a disease, disorder, or side effect, or a decrease in the rate of advancement of a disease or disorder. The term also includes within its scope amounts effective to enhance normal physiological function.

The present invention is further illustrated by the following examples, which are provided for the purpose of demonstration rather than limitation.

EXAMPLES

Statistical Analysis

Data obtained from animal experiments were expressed as the means and standard deviation of the means (±S.D.M). Student's t-test was used to examine the differences among multiple groups or between two groups. Statistical significance is expressed as * $p<0.05$,  $p<0.01$ and * $p<0.001$.

Example 1

1.1 Preparations of FT Compositions

By way of example, any of the FT compositions set forth in Table 1 can usefully be prepared to provide the dissolution, bioaccessibility, absorption, and pharmacokinetic analyses. The FT compositions were prepared from the ingredients including 1-20% T3, 1-20% carrier, 1-5% surfactant, 52-94% filler(s), such as isomalt, starch, lactose, cyclodextrin, isomaltodextrin, lactose+isomalt, lactose+maltodextrins, and lactose+cyclodextrins, and 3% binder (Table 1). The oil phase components, including T3 and surfactant, and the solid phase excipients, including carrier and filler, were well mixed separately. The solid phase excipients were added to the oil phase solution and well mixed. The binder was dissolved in a solvent, such as ethanol, and then added to and well mixed with the solid phase. Alternatively, the binder could be directly added to and mixed with the solid phase. The mixture was sieved and dried, and then passed through a mesh.

TABLE 1

SESD T3 compositions

| Compositions | API 1-20% | Carrier 1-20% | Surfactant 1-5% | Filler 52-94% | Binder 3% | Physical properties |
|---|---|---|---|---|---|---|
| FT1 | T3 | SiO$_2$ | TWEEN ® 80 | Isomalt | PVP K30 | +++ |
| FT2 | T3 | SiO$_2$ | TWEEN ® 80 | Starch | PVP K30 | |
| FT3 | T3 | SiO$_2$ | TWEEN ® 80 | Lactose | PVP K30 | +++ |
| FT4 | T3 | SiO$_2$ | TWEEN ® 80 | Isomalt | PVP K30 (un-wet granulation) | +++ |
| FT5 | T3 | SiO$_2$ | TWEEN ® 80 | Starch | PVP K30 (un-wet granulation) | +++ |
| FT6 | T3 | SiO$_2$ | TWEEN ® 80 | Cyclo-dextrin; | PVP K30 | +++ |
| FT7 | T3 | SiO$_2$ | TWEEN ® 80 | Isomalto-dextrin; | PVP K30 | +++ |
| FT8 | T3 | SiO$_2$ | TWEEN ® 80 | Lactose+Isomalt | PVP K30 | +++ |
| FT9 | T3 | SiO$_2$ | TWEEN ® 80 | Lactose+Malto-dextrins; | PVP K30 | +++ |
| FT10 | T3 | SiO$_2$ | TWEEN ® 80 | Lactose+Cyclo-dextrins; | PVP K30 | +++ |

Physical Properties:

+++: Indicates that the sample has a powdery appearance, but it has good fluidity and is not easy to absorb moisture.

++: Indicates that the sample has a powdery appearance, but the fluidity is acceptable or fair, and it is not easy to absorb moisture and moisture.

+: Indicates that the sample has a powdery appearance, but the fluidity is poor, or it is easy to absorb moisture and moisture.

–: Indicates that the sample has a powdery appearance, but there is also a partial sticky substance.

––: Indicates that the sample cannot form a powder, and it is like a muddy paste.

1.2 Selection of Carriers

A selection of carriers suitable for the preparation of SESD composition was prepared with a constant amount of T3 (50%), and the carriers (50%) included SiO$_2$, calcium silicate, PVP polymers and copolymers, maltodextrins, isomalt, and cyclodextrin (Table 2). Based on the results showed in Table 2, the composition consisting of T3 and SiO$_2$ exhibited the best physical properties.

TABLE 2

Selection of carriers

| Compositions | API | Carrier | Physical properties |
|---|---|---|---|
| FT11 | T3; 50% | SiO$_2$; 50% | +++ |
| FT12 | T3; 50% | Calcium Silicate; 50% | + |
| FT13 | T3; 50% | PVP polymers and copolymers; 50% | –– |
| FT14 | T3; 50% | Malto-dextrins; 50% | –– |
| FT15 | T3; 50% | Isomalt; 50% | – |
| FT16 | T3; 50% | Cyclo-dextrin; 50% | – |

Physical properties:

+++: Indicates that the sample has a powdery appearance, but it has good fluidity and is not easy to absorb moisture.

++: Indicates that the sample has a powdery appearance, but the fluidity is acceptable or fair, and it is not easy to absorb moisture and moisture.

+: Indicates that the sample has a powdery appearance, but the fluidity is poor, or it is easy to absorb moisture and moisture.

–: Indicates that the sample has a powdery appearance, but there is also a partial sticky substance.

––: Indicates that the sample cannot form a powder, and it is like a muddy paste.

Based on the ratio of T3 and SiO$_2$ shown in the Table 3, the FT compositions were prepared to determine the physical properties. As shown in Table 3, all FT compositions exhibited good physical properties.

TABLE 3

Formulations of FT compositions consisting of T3 and SiO$_2$

| Compositions | API | SiO$_2$ | Physical properties |
|---|---|---|---|
| FT18 | T3; 70% | 30% | + |
| FT19 | T3; 60% | 40% | +++ |
| FT11 | T3; 50% | 50% | +++ |
| FT21 | T3; 20% | 80% | +++ |

Physical properties:

+++: Indicates that the sample has a powdery appearance, but it has good fluidity and is not easy to absorb moisture.

++: Indicates that the sample has a powdery appearance, but the fluidity is acceptable or fair, and it is not easy to absorb moisture and moisture.

+: Indicates that the sample has a powdery appearance, but the fluidity is poor, or it is easy to absorb moisture and moisture.

–: Indicates that the sample has a powdery appearance, but there is also a partial sticky substance.

––: Indicates that the sample cannot form a powder, and it is like a muddy paste.

Example 2

Dissolution Tests of UNF and Various FT Compositions 2.1 Dissolution Test Procedures The FT compositions and UNF T3, including 2.0 g formulated powder or 150 mg oil form, were exposed to 750 mL of the acid medium (0.025% SDS-HCl aqueous solution, prepared by dissolving 2.5 g of sodium dodecyl sulfate (SDS) and 83 mL of hydrochloric acid in 10 L of purified water, pH 1.2) followed by exposure to the buffer medium (sequentially add 250 mL of 0.20 M tribasic sodium phosphate to the fluid in the vessel with a total volume was equal to 1000 mL). The dissolution tests were performed in the media with pH 1.2 and 6.8 sequentially. The test solutions in the acid medium were sampled and filtered at 15 and 30 minutes, respectively, through a 0.45 μm syringe filter. After 30 minutes, 250 mL of 0.20 M tribasic sodium phosphate was added to form a buffer medium. Next, the test solutions were sampled after 30 minutes and filtered through a 0.45 μm syringe filter. The collected media were subjected to HPLC (High Performance Liquid Chromatography) or MS (Mass spectrometry) analysis of T3 release rate.

2.2 Results

Figure 1:
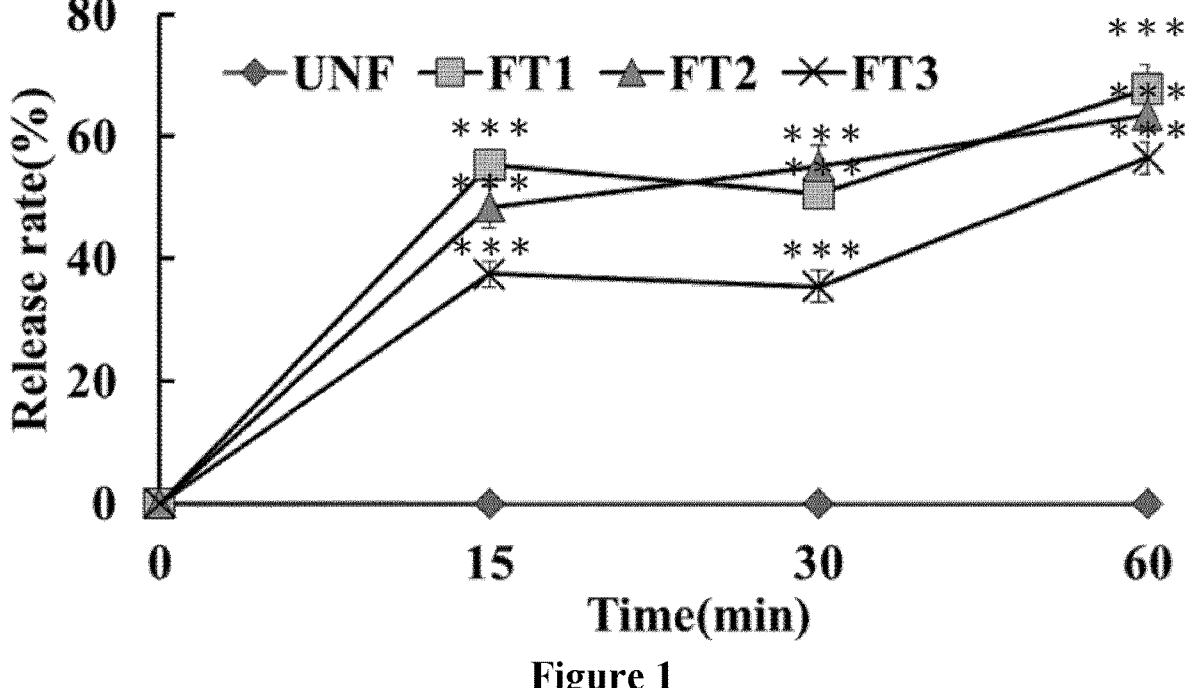
FIG. 1 shows the T3 release rates of different formulated T3 (FT) compositions with the dissolution assay. Three compositions, including F T1, FT2, and FT3, show significantly higher T3 release rates at pH 1.2 and pH 6.8 compared with UNF. UNF, unformulated T3; FT1, isomalt+wet granulation; FT2, starch+wet granulation; FT3, lactose+wet granulation. Data is presented as means±SD, n=3 for each group; ***, p<0.001.

The dissolution analysis of UNF and various FT T3 was determined at pH values of 1.2 and 6.8 under which stomach and small intestines digest, respectively. The results showed that T3 dissolution from FT1, FT2, and FT3 compositions significantly increased at both pH values of 1.2 and 6.8 compared with that of UNF (FIG. 1). Actually, T3 dissolution from the control UNF group at both pH values of 1.2 and 6.8 could barely be detected.

Example 3

Bioaccessibility (Transcellular Absorption) Analysis Using Caco-2 Cell Model.

3.1. Cell Culture

To investigate the transcellular absorption of T3 by enterocytes, Caco-2 cell model was used. Caco-2 cells were seeded to 0.4 μm transwell insert in 12 well plate. 1 mL of medium was added to the basolateral compartment and 0.5 mL of medium to the apical compartment. The cells were allowed to evenly distribute and attach to the plate button, and incubated at 37° C. with an atmosphere of 5% $CO_2$ and 95% air.

3.2. Differentiation of Caco-2 Cell Lines

Caco-2 cells started to differentiation spontaneously when the cells reached 80% confluence and after a total culture period of around 14-21 days they appeared dense microvilli on the apical side, characteristic of small intestinal enterocytes. To ensure the proper differentiation of culture cells, Trans-Epithelial Electrical Resistance (TEER) values were measured. The cultured cells with the values between 2500-4000 by Ohm Meter were used for study.

3.3. Treatment with UNF or Various FT T3s

Cells were washed with PBS before treatment. Then UNF and various FT T3s were added into the transwell insert, and cells were incubated for 2 h.

3.4. Media Collection and Analysis

The media were collected form the apical and basolateral chamber and transferred to the 1.5 ml eppendorf. Then, the T3 in the media ware analyzed by mass spectrometry (MS).

3.5 Results

Figure 2:
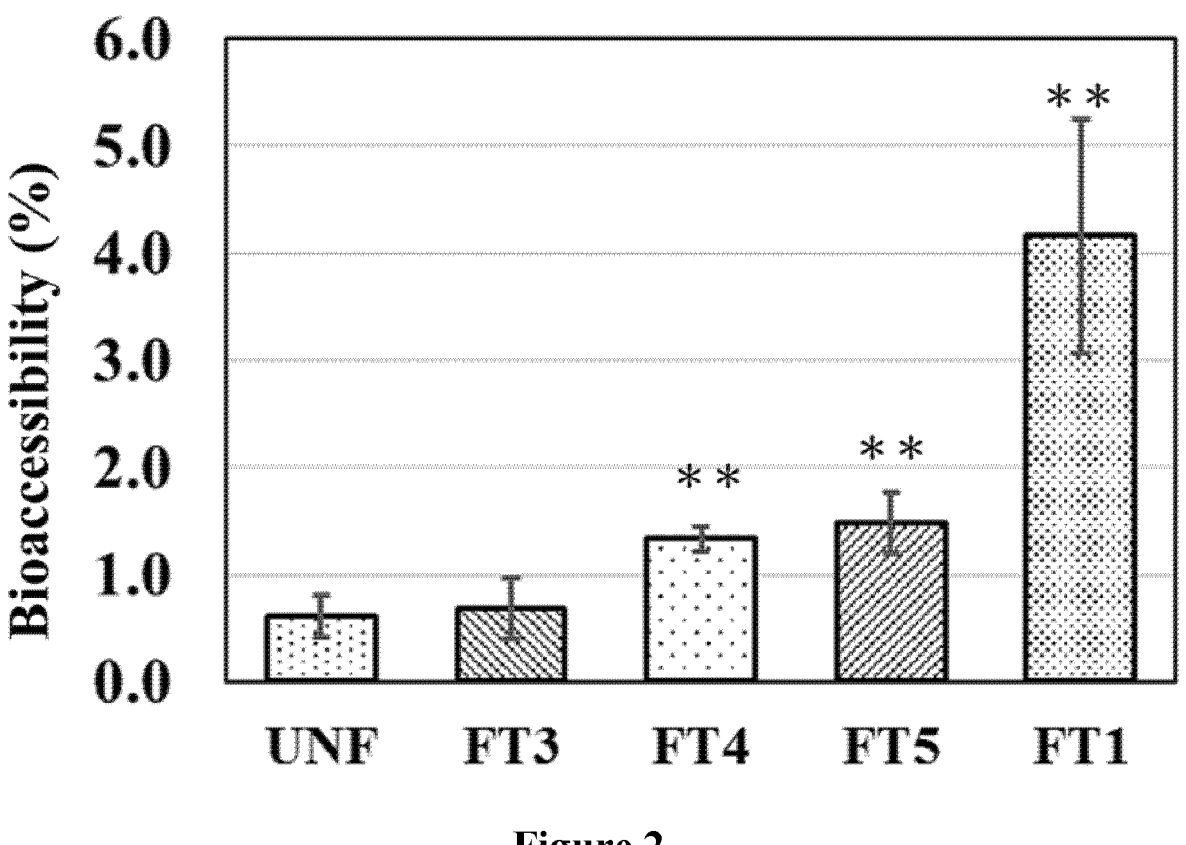
FIG. 2 shows a bioaccessibility (transcellular absorption) analysis of UNF and different FT compositions in Caco-2 cell monolayer model. Of five formulated T3 (FT) compositions applied to Caco-2 monolayer, four FT compositions show significantly increased their bioaccessibility compared with UNF. UNF, unformulated T3; FT1, isomalt+wet granulation; FT3, lactose+wet granulation; FT4, isomalt+PVP K30; FT5, starch+PVP K30. Data is presented as means±SD, n=3 for each group; *, p<0.05, **, p<0.01.

The T3's flux and apparent bioaccessibility coefficients across Caco-2 cell monolayers obtained were shown in FIG. 2. As demonstrated in FIG. 2, FT1, FT4 and FT5 compositions significantly increased the absorption of T3 across Caco-2 monolayers as compared with UNF. However, similar result was found between FT3 and UNF.

Example 4

Absorption of T3 in Hepatocytes Using HepaRG Cells Model 4.1 Cell Culture

HepaRG cells were seeded in 6 well plate filled with 2 mL of medium, and incubated at 37° C. with an atmosphere of 5% $CO_2$ and 95% air.

4.2. Treatment with UNF or Various FT T3s.

Cells were washed with PBS before the adding of T3 compositions. Then, UNF or various FT T3s were added into the plate, respectively, and cells were incubated for 6 h.

4.3. Media Collection and Analysis

The media were collected, and HepaRG cells were pelleted and lyzed to obtain the cell proteins. Then the media and cell proteins were analyzed by MS.

4.4 Results

Figure 3:
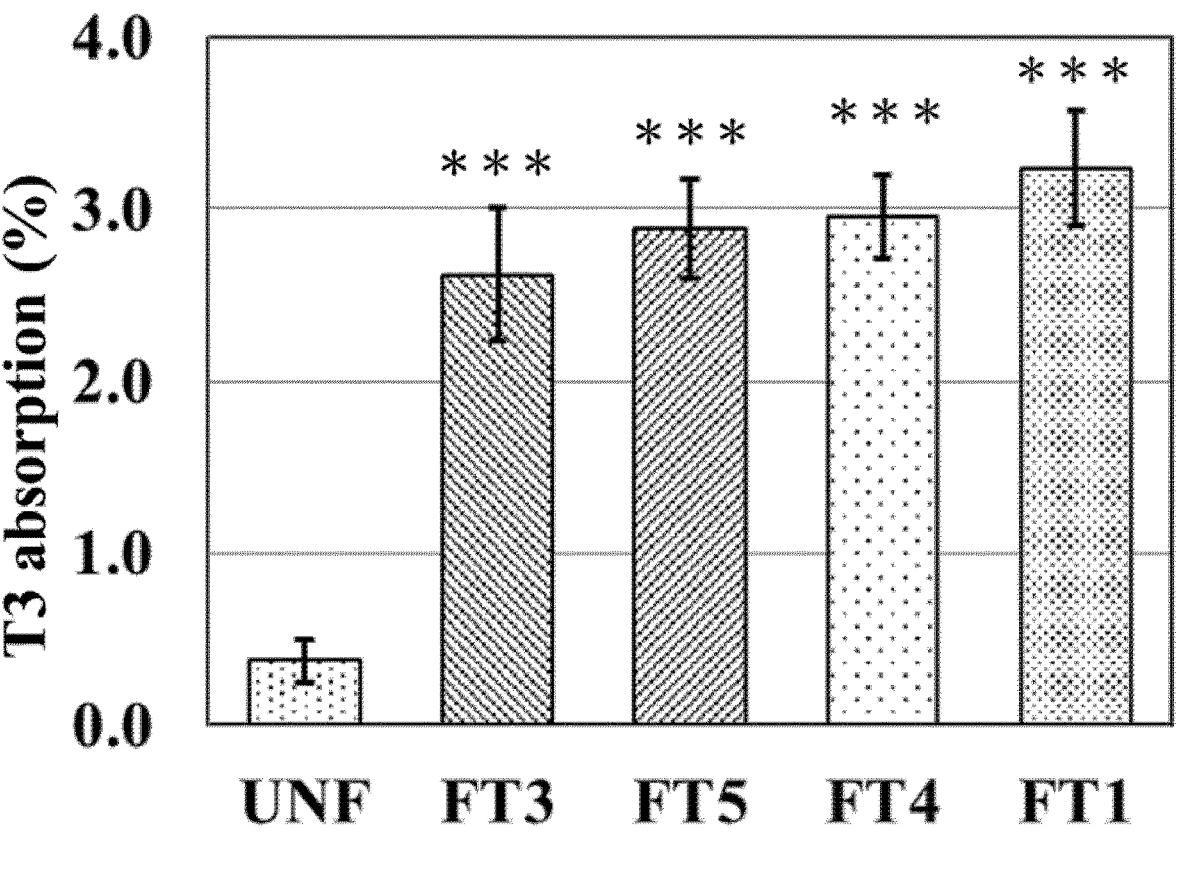
FIG. 3 shows the absorption rates of different FT compositions in HepaRG cells. Using HepaRG cell assay, all FT compositions have T3 absorption rates significantly higher than that of UNF. UNF, unformulated T3; FT1, isomalt+wet granulation; FT3, lactose+wet granulation; FT4, isomalt+

To investigate the functions of T3 hepatic uptake, an absorption study with HepaRG cells was performed using UNF and various FT T3s, including FT1, FT3, FT4, and FT5. Compared to UNF, significantly higher T3 absorption of FT1, FT3, FT4, and FT5 could be observed in HepaRG cells (FIG. 3).

Example 5

Pharmacokinetic (PK) Analysis Using Sprague Dawley (SD) Rats Model 5.1 Animal

SD rats (male, 250-400 g, about 8-9 weeks) were used in this experiment. After 12-hour starving, one group of SD rats were fed with UNF (raw material, unformulated) and the other rats were fed with TF1 (formulated T3).

5.2 Treatment with UNF or TF1

One dose of either UNF or TF1 was fed to SD rat, respectively. The content of T3 in TF1 in one feeding dose was similar to that of UNF (36 mg T3, measured by MS, for both groups).

5.3 Blood Collection and Analysis

Blood was collected from the tail vein at 0, 0.5, 1, 2, 4, 6, and 12 hours, and the serum was centrifuged for HPLC or MS analysis of T3 content.

5.4 Results

Comparative pharmacokinetic study of UNF and TF1 in SD rats were shown in FIG. 4. After oral supplementation (one dose of 36 mg T3, formulated or unformulated) to SD rats, Tmax, Cmax and AUC of SD rats with TF1 treatment were markedly superior to those of SD rat with UNF treatment (Cmax: TF1 1.59±0.10 ppm vs UNF 0.71±0.06 ppm; AUC: TF1 4.97±0.89 vs UNF 2.75±0.24). These results may indicate that oral administration of TF1 has superior pharmacokinetic profiles compared to those of UNF.

The results in the in vitro Caco-2 cell model indicate that the SESD T3 compositions significantly increase the bioaccessibility (transcellular absorption) of Caco-2 enterocytes compared with the unmodified prototype of T3s. So do the results of absorption in the HepaRG hepatocyte model, as well as the results of PK study in SD rats.

In addition, in the dissolution tests, each of the SESD compositions of T3 had a significantly increase in solubility compared with the unmodified prototype of T3 at both pH values (1.2 and 6.8) under which stomach and small intestines digest, respectively. Therefore, chemically the SESD compositions significantly improved the hydrophilicity of lipophilic T3 and biologically its bioaccessibility or absorption in the intestine, liver and in vivo test.

The above description merely relates to preferred embodiments in the present invention, and it should be pointed out that, for a person of ordinary skill in the art, some improvements and modifications can also be made under the premise of not departing from the principle of the present invention, and these improvements and modifications should also be considered to be within the scope of protection of the present invention.

What is claimed is:

1. A method for increasing bioaccessibility and hepatic uptake of a tocotrienol in a subject, comprising:
administering orally to the subject a composition consisting of (a) a tocotrienol, (b) polysorbate 80 as a surfactant, (c) silicon dioxide (SiO$_2$) as a carrier, (d) isomalt as a carbohydrate filler, and (e) polyvinylpyrrolidone (PVP) K30 as a binder, wherein the polysorbate 80 as the surfactant is present in a percentage by weight of 1% to 5%, the SiO$_2$ as the carrier is present in a percentage by weight of 0.1%-20%, the isomalt as the carbohydrate filler is present in a percentage by weight of 40%-90%, and the PVP K30 as the binder is present in a percentage by weight of 3%, and wherein the composition is prepared by wet granulation;
thereby increasing bioaccessibility and hepatic uptake of the tocotrienol in the subject.

2. A method for increasing bioaccessibility and hepatic uptake of a tocotrienol in a subject, comprising:
administering orally to the subject a composition consisting of (a) a tocotrienol, (b) polysorbate 80 as a surfactant, (c) silicon dioxide (SiO$_2$) as a carrier, (d) isomalt as a carbohydrate filler, (e) polyvinylpyrrolidone (PVP) K30 as a binder, and (f) a lubricant: wherein the polysorbate 80 as the surfactant is present in a percentage by weight of 1% to 5%, the SiO$_2$ as the carrier is present in a percentage by weight of 0.1%-20%, the isomalt as the carbohydrate filler is present in a percentage by weight of 40%-90%, and the PVP K30 as the binder is present in a percentage by weight of 3%, and wherein the composition is prepared by wet granulation;
thereby increasing bioaccessibility and hepatic uptake of the tocotrienol in the subject.

* * * * *